United States Patent [19]
Patil et al.

[11] Patent Number: 6,015,699
[45] Date of Patent: Jan. 18, 2000

[54] PROCESS FOR THE PRODUCTION OF ALCOHOL

[75] Inventors: Shamrao Ganpatrao Patil; Bhaskar Ganpatrao Patil; Digambar Vitthal Gokhale; Kulbhushan Balwant Bastawde; Ulka Shrirang Puntambekar; Prabhakar Kamalakar Ranjekar, all of Maharashtra, India

[73] Assignee: Council of Scientific & Industrial Research, New Delhi, India

[21] Appl. No.: 09/047,988

[22] Filed: Mar. 25, 1998

[30] Foreign Application Priority Data

Sep. 30, 1997 [IN] India ........................................ 2783/97

[51] Int. Cl.⁷ ................................ C12P 7/06; C12P 7/08; C12P 7/010
[52] U.S. Cl. ........................ 435/161; 435/163; 435/164; 435/165; 435/940; 435/942
[58] Field of Search ..................... 435/161, 163, 435/164, 165, 940, 942

[56] References Cited

PUBLICATIONS

Derwent Abstract WPIL 86–241856/37 Nakasone JP61170380, Aug. 1, 1986.
Derwent Abstract WPIL 86–249467/38 Tashiro JP61177974, Aug. 9, 1985.
Derwent Abstract WPIL 94–275511/34 Tokusa JP06205664, Jul. 26, 1994.
Derwent Abstract WPIL 90–336363/45 Broussous et al WP–395822, Nov. 7, 1990.
Derwent Abstract WPIL 88–113128/17 Schubert et al DD–251990, Dec. 2, 1987.
Derwent Abstract WPI 75–73549W/44 Food Ind Des Bur SU–448221, Dec. 15, 1974.
Biotech Abstract 97–08684 Srivastava et al "Production of Ethanol from Guava Pulp by Yeast Strains" Biores. Biotechnol (1997)60,3,263–65.

*Primary Examiner*—Herbert J. Lilling
*Attorney, Agent, or Firm*—Abelman, Frayne & Schwab

[57] ABSTRACT

The subject invention relates to an improved process for the production of alcohol which obviates the drawbacks and limitations of the hitherto known process, comprises growing a yeast in a conventional growth medium, fermenting the medium containing carbon and nitrogen source along with other conventional nutrient ingredients and fruit supplement in whole or in fractions like husk, pulp, powder of seeds and mixture thereof used at least 0.25% by weight allowing the resultant broth to ferment for at least 15 hours at temperature in the range of 15–37° C.

3 Claims, No Drawings

PROCESS FOR THE PRODUCTION OF ALCOHOL

The present invention relates to a process for the production of alcohol. More particularly it relates to the production of alcohol by fermentation using added fruit supplementation in fermentation medium. The fermentation medium contains the source of carbohydrates like molasses sugar, along with other conventional ingradients for supply of nitrogen. The yeast cultures used for the fermentation are such as Sacch. cerevisiae and Sacch. uvarum.

In India, conventional batch fermentation is in practice. Normally the cane molasses sugar concentration (TRS) 15% is used for the production of alcohol by using yeast inoculum size around 10% (v/v). It is noticed that after a period of 24 hours of fermentation, distillaries are able to get 7.0–8.0 (v/v) alcohol with maximum efficiency of 80%. All these conditions again depend upon the grade of molasses used. This particular solvent, a alcohol is an important organic solvent and starting agent for many organic synthesis. Secondly it is a valuable alternate source of energy in place of petroleum. No doubt it is largely produced by synthetic methods and also produced by the old method of yeast fermentation using waste materials like pulp, starches, cane molasses, whey etc. Supplementation of ergosterol (Anderson, A. A. and Stier T. J. B. J. Cell Comp Physiol. 41, 23–26 1953), skim milk powder (Patil S. G. et al Enzyme Microb. Technol 8, 481–486 1966), chitin (Patl S. G., and Patil B. G. Enzyme Microb Technol. 11, 38–43 1989), fungal mycelium (Patil, S. G. and Patil, B. G. Enzyme Microb Technol 12, 141–148, 1990) and proteolipids (Hayshida, S. and Ohta K. Agric. Biol. 42, 1139–1145, 1978) has shown improvement in alcoholic fermentation. New techniques such as the use of top and bottom yeast (Patil, S. G. and Patil B. G., Biotechnol. Lett. 11: 359–634, 1989) vacuum fermentations (Ramalingham, A. and Finn, R. K. Biotech. Bioeng. 12, 583–289 1977), rapid fermentation (Nagodawihana, T. W. Castelliano, C. and Steinkraus, K. H., Appl. Microbiol. 28, 383–391 1974), cell recycling (Sedha R. K. et. al J. Ferment Technol. 62, 471–476 1984), continuous fermentation (Cysewski G. R. and Wike, C. R. Bioetech. Bioeng. 20, 1421–1444 1978), whole cell immobilization (SivaRaman, H. et al Biotech. Lett. 4, 359–364 1982) have been reported for alcohol production.

The main objective of the present invention is to provide an improved process for the production of alcohol which obviates the drawbacks and limitations of the hitherto known process. Another objective of the present invention is to provide an improved process wherein fruits' supplementation is used in the fermentation medium to accelerate and to increase the yield of alcohol production. Yet another objective of the present invention is to provide an economical, feasible process for the production of alcohol.

Accordingly the present invention provides an improved process for the production of alcohol which comprises of growing a yeast saccharomyces sp. in a conventional growth medium and fermenting the medium containing carbon and nitrogen source along with other conventional nutrient ingradients and fruit supplement like banana (*Musa paradisiaca*), chiku (Sapota, *Achras sapotaa*), custard apple (*Annona squamosa*), mosambi (*Citrus sinensis*), orange (*Citrus reticulata*), apple (*Matus sylvestris*), pine apple (*Ananas sativus*), popaya (*Carica papaya*), guava (*Psidium guavava*), ber (*Zyzpus jujuba*), pomegranate (*Punica granmatum*), mango (*Mangifera indica*) and tamarind (*Tamarindus indica*), in whole or fractions like husk, pulp, powder of seeds and mixture there of used at least 0.25% by weight allowing the resultant broth to ferment for atleast 15 hours at temperature in the range of 15–37° C. recovering and estimating the alcohol by known method.

We have, during the course of our research, observed that the supplementation of fruits such as banana (*Musa paradisiaca*), chiku (Sapota, *Achras sapotaa*), custard apple (*Annona squamosa*), mosambi (*Citrus sinensis*), orange (*Citrus reticulata*), apple (*Malus sylvestris*), pine apple (*Ananas sativus*), popaya (*Carica papaya*), guava (*Psidium guavava*), ber (*Zyzypus jujuba*), pomegranate (*Punica granmatum*), mango (*Mangifera indica*) and tamarind (*Tamarindus indica*) or their fractions in fermentation medium resulted in improved alcoholic fermentation process. Supplementation of fruit has not only improved the rate of alcohol production but showed increased percentage of alcohol from appropriate sugar concentration in alcoholic batch fermentation.

The following parameters were used for the production of alcohol. Industrially used microorganisms specifically *Saccharomyces cerevisiae* or *Saccharomyces uvarum* have been employed. Different types of sugars available from various sources like cane molasses sugars, cane juice, grape juice and glucose were used. Fermentation process can be carried out in batch, fed batch, continuous or allied processes. An improved process for the production of alcohol which comprises growing a Saccharomyces sp. in conventional growth medium such as MGYP (glucose—5.0%; malt extract—0.3%, yeast extract—0.3% and peptone—0.5%) or another cheaper growth medium MUMY (molasses sugar concentration 5.0–6.0%, urea 0.1% magnesium sulphate 0.05% and yeast extract 0.1%). The required inocula was build up growing yeast culture at 28–30° C. for 24 hours on shaking condition (150 RPM). The fermentation medium used may be such as (carbon sources atleast 15% and nitrogen sources like urea 0.2%, magnesium sulphate 0.05% and yeast extract 0.1% specifically for cane molasses fermentation. For other fermentation medium such as glucose, sucrose, cane juice or grape juice, and salts are incorporated like ammonium sulphate 0.1%, urea 0.2%, potassium di-hydrogen phosphate 0.1%, magnesium sulphate 0.05% and yeast extract 0.1% by keeping pH 5.0) were used. All the fennentation media were supplemented with fruits or their fractions more than 0.2%. All thes media were autoclaved at 15 lb for 20 min. Allowing the resultant broth to ferment atleast 15 hours at a temperature in the range of 15–37° C., recovering the alcohol by known methods such as distillation and then alcohol was estimated chemically or by HPLC methods. While the total reducing sugars were estimated after the hydrolysis with HCl by dinitrosalicylic acid (DNS) method.

In this present invention industrially used Saccharoitiyces sp. is selected from *Saccharomyces cerevisiae* or *Saccharomyces uvarum*, having the same characteristics as that of ATCC No. 26602.

In an embodiment of the present invention the fruit supplement used in the fermentation medium may be selected from banana (*Musa paradisiaca*), chiku (Sapota, *Achras sapotaa*), custard apple (*Annona squamosa*), mosambi (*Citrus sinensis*), orange (*Citrus reticulata*), apple (*Malus sylvestris*), pine apple (*Ananas sativus*), popaya (*Carica papaya*), guava (*Psidiumin guavava*), ber (*Zyzypus jujuba*), pomegranate (*Punica granmatum*), mango (*Mangifera indica*) and tamarind (*Tamarindus indica*), in whole or fractions like husk, pulp, powder of seeds and mixture there of may be used at least 0.25% by weight.

The present invention provides the potential invention of fruits or their fractions as supplement to be added in small quantity during fermentation which stimulates the rate of alcohol production and secondly shows more production of alcohol from increased concentration of glucose in alcoholic fermentation.

The following examples are given by way of illustrations of the process of the present invention and therefore should not be construed to limit the scope of the present invention.

EXAMPLE 1

Glucose Fermentation: Initially the effect of thirteen fruits available throughout the season or their fractions (mentioned in the Table 1) has been evaluated individually for the production of alcohol. Initialy, the fermentation medium (90 ml in 100 ml conical flask) containing 25% glucose and required salts has been selected for experiment. The fermentation media supplemented with 2% of fruit were inoculated with 10% homogenous inoculum of S. cerevisiae, pregrown, in conventional MGYP growth medium at 30° C. A control flask was also run without the addition of any fruit supplement. All these flasks were left stationary at 30° C. Samples (5ml) were removed from fermented flask for alcohol estimation after a period of 48 h. and 72 h.

TABLE 1

Glucose Fermentation
Glucose: 25% with Am. sulphate 0.1%, urea 0.2%, pot. di hydro phosphate 0.1%, magnesium sulphate 0.05% and yeast extract 0.1%.
Yeast culture: S. cerevisiae, Yeast inoculum: 10% (v/v)
Temperature: 30° C., pH: 5.5, Total volume: 100 ml
Supplement of fruit used: 2.0%

| Sr. No | Supplement | Estimated Alcohol (w/v) at | | | |
|---|---|---|---|---|---|
| | | 48 h | % IMP | 72 h | % IMP |
| 1. | Control | 4.15 | — | 6.25 | — |
| 2. | Banana | 6.85 | 65 | 9.80 | 56 |
| 3. | Chiku | 6.90 | 66 | 10.15 | 62 |
| 4. | Mosumbi | 5.25 | 26 | 7.25 | 16 |
| 5. | Orange | 5.35 | 29 | 7.60 | 21 |
| 6. | Custard apple | 6.95 | 67 | 10.20 | 64 |
| 7. | Apple | 6.85 | 65 | 9.80 | 56 |
| 8. | Pineapple | 6.90 | 66 | 10.00 | 60 |
| 9. | Popaya | 6.75 | 62 | 9.50 | 52 |
| 10. | Pomogranate | 6.50 | 56 | 9.75 | 56 |
| 11. | Gauva | 6.55 | 57 | 10.15 | 62 |
| 12. | Ber | 6.65 | 60 | 9.25 | 50 |
| 13. | Mango | 7.10 | 71 | 11.00 | 76 |
| 14. | Tamarind fruit | 6.10 | 47 | 9.20 | 47 |
| 15. | Tamarind husk | 6.35 | 53 | 9.10 | 45 |
| 16. | Tamarind pulp | 6.50 | 56 | 8.75 | 40 |
| 17. | TSP | 6.40 | 54 | 9.65 | 54 |

% IMP. = Percent Improvement,
TSP = T. seed powder

As seen from table 1 the fruit supplemented fermentation flasks showed improvement in alcohol production in the range of 30–70% as compared to control at 48 h. The similar pattern of improvement was observed at 72 h. It is also observed that the fermentation activity is nearly reached to its completion in the fruit supplemented media at 72 h. while the control required more period for the completion. Out of all the fruits added, banana, chiku, custard apple and mango were found more effective in alcoholic fermentation. Overall 85% efficiency is observed.

EXAMPLE 2

Grape Juice Fermentation: Locally available grapes, white and red grade, were collected and grape juice was collected by 1:1 ratio with water after steaming for 30 minutes. Glucose was added to grape juice to get final glucose concentration of 25%, followed by the addition of the required salts. The fermentation was carried out as described in example No. 1. Instead of taking all the fruits, four fruits, banana, chikku, mosambi and apple were selected as supplements (2.0%) to study the effect on fermentation activity.

TABLE 2

Grape Juice Fermentation
Grape juice: 25% made up with the addition of glucose. Addition of salts same as Table 1.
Yeast culture: S. cerevisiae
Yeast inoculum: 10% (v/v) Temperature: 30° C. pH: 5.5
Total volume 100 ml
Supplement of fruit used: 2.0%

| Sr. No. | Supplement | Estimated Alcohol (w/v) at | | | |
|---|---|---|---|---|---|
| | | 48 h | % IMP | 72 h | % IMP |
| Grapes used are of White Grade | | | | | |
| 1. | Control | 6.5 | — | 8.35 | — |
| 2. | Banana | 9.5 | 46 | 10.80 | 29 |
| 3. | Chiku | 9.25 | 42 | 10.65 | 27 |
| 4. | Mosumbi | 8.00 | 23 | 10.70 | 28 |
| 5. | Apple | 8.10 | 24 | 10.85 | 29 |
| Grapes used are of Red Grade | | | | | |
| 1. | Control | 6.10 | — | 7.85 | — |
| 2. | Banana | 9.60 | 57 | 10.95 | 39 |
| 3. | Chiku | 9.25 | 51 | 10.00 | 27 |
| 4. | Mosumbi | 8.15 | 33 | 9.75 | 24 |
| 5. | Apple | 8.30 | 36 | 9.25 | 26 |

IMP. = Percent Improvement

It is observed from Table 2 that the fermentation flasks supplemented with fruits improved the rate of alcohol formation. The alcohol production was also improved in the range of 23–46% for white grape juice, and 33–57% for red grape juice when estimated at 48 hrs as compared to their respective controls in absence of fruit supplementation. When the fermentation was continued further improvement was recorded 28% and 30% for white grapes and red grape juice respectively. In the presence of supplements the fermentation is completed at 72 h with 86% efficiency while unsupplemented flask takes more time for its completion.

EXAMPLE NO. 3

Fermentation with molasses sugars: Locally available cane molasses with 55% total reducing sugars and 14% other salts was used. The total reducing sugar was adjusted to required percentage (24%) by diluting with water and pH was adjusted with NaOH or, HCl to 5.5 and was steamed for 30 min. The salts like urea, magnesium sulphate and yeast extract were added to diluted molasses. The yeast inocula and fermentation procedure was followed as given in example No 1. The fruits like banana, chiku and tamarind and their fractions were added as supplements to evaluate the fermentation activity.

TABLE 3

Fermentation with molasses sugars
Total Molasses: Reducing Sugar 24% with urea 0.2%,
magnesium sulphate 0.05% and yeast extract 0.1%
Yeast culture: S. cerevisiae    Yeast inoculum: 10% (v/v)
Temperature: 30° C., pH: 5.5
Total volume 100 ml
Spplemelt of fruit used: 2.0%

| Sr. No. | Supplement | \multicolumn{6}{c}{Estimated Alcohol (w/v) at} |
|---|---|---|---|---|---|---|---|

| Sr. No. | Supplement | 48 h | % IMP | 72 h | % IMP | 120 h | % IM |
|---|---|---|---|---|---|---|---|
| 1. | Control | 3.45 | — | 6.85 | — | 7.05 | — |
| 2. | Banana | 7.70 | 123 | 10.05 | 47 | 10.00 | 41 |
| 3. | Chiku | 8.35 | 140 | 10.25 | 49 | 10.00 | 41 |
| 4. | Tamarind | 7.60 | 120 | 9.15 | 33 | — | — |
| 5. | T. husk | 7.40 | 114 | 9.60 | 40 | — | — |
| 6. | T. pulp | 7.45 | 115 | 9.55 | 39 | — | — |
| 7. | T. seed | 7.35 | 113 | 9.45 | 37 | — | — |

% IMP: Percent Improvement, T.: Tamarind

From Table 3 it has been observed that ethanol produciton is improved remarkably in a range of 123–140% at 48 hr. and 33–49% at 72 hrs. in the presence of fruit supplementation or their fractions. The production of ethanol has been improved at 72 hours in the presence of fruits like banana, chiku and tamarind fruit or their fractions as compared to a control in absence of supplements. It is noticed that the fermentation activity is completed in the presence of fruit supplementation while the control requires more days to reach the completion stage.

EXAMPLE NO. 4

Fermentation using S. uvarum culture: The other industrially used yeast culture like Saccha. uvarum has been used in alcoholic fermentation medium containing 25% glucose along with all the other required salts. The fermentation procedure remains same as in example No. 1, in the presence of selected supplement like banana, chiku, mosumbi, custard apple and apple.

TABLE 4

Fermentation Using S. uvarum culture
Glucose: 25% with addition of salts same as Table 1
Yeast culture: S. uvarum NCIM 3509 Yeast inoculum: 10% (v/v)
Temperature 30° C. pH: 5.5 Total volume: 100 ml
Supplement of Fruit used: 2.0%

| Sr. No. | Supplement | 48 h | % IMP | 72 h | % IMP |
|---|---|---|---|---|---|
| 1. | Control | 4.55 | — | 6.35 | — |
| 2. | Banana | 6.65 | 46 | 10.20 | 60 |
| 3. | Chicku | 6.95 | 52 | 10.25 | 61 |
| 4. | Mosumbi | 5.95 | 30 | 9.95 | 56 |
| 5. | Custard apple | 7.00 | 53 | 11.00 | 73 |
| 6. | Apple | 6.75 | 48 | 10.05 | 58 |

% Imp = Percent Improvement

It is observed from Table 4 by employing the yeast culture like Sacch. uvarum, the ethanol production has been improved by 53–59% in the presence of supplements at 48 h. of fermentation period as compared to its control. It is further noticed that the improvement was continued up to 72 hrs (56–65%) at which the fermentation was completed. The results obtained by using S. uvarum were found to be similar to those obtained with culture S. cerevisiae used in example no. 1.

We claim:

1. An improved process for the production of alcohol which comprises growing yeast saccharomyces sp. in a conventional growth medium of MGYP and a fermenting medium containing carbon and nitrogen sources and at least 0.25% by weight on dry weight of fruit supplements selected from the group consisting of banana (*Musa paradisiaca*), chiku (Sapota, *Achras sapotaa*), custard apple (*Annona sqamosa*), mosambi (*Citrus sinensis*), orange (*Citrus reticulata*), apple (*Malus sylvestris*), pineapple (*Ananas sativus*), papaya (*Carica papaya*), guava (*Psidium guavava*), ber (*Zyzypus jujuba*), pomegranate (*Punica granmatum*), mango (*Mangifera indica*) and tamarind (*Tamarindus indica*), in the form of the whole fruit, or the husk, pulp, or a powder and mixtures thereof; allowing the resultant broth to ferment for at least 15 hours at a temperature in the range of 15–37° C.; and recovering the alcohol.

2. An improved process as claimed in claim 1 wherein the fermentation media has at least a 25% concentration of a member selected from the group consisting of molasses, sugars, glucose, grape juice or cane juice and the starting pH is 5.5.

3. An improved process as claimed in claim 1 wherein the yield of alcohol increases between about 25% and about 150% depending on the fruit supplement employed.

* * * * *